United States Patent [19]

Singer

[11] Patent Number: 5,082,445
[45] Date of Patent: Jan. 21, 1992

[54] OSTEOINTEGRATED IMPLANTS AND DENTAL IMPLANT ASSEMBLIES

[76] Inventor: Shmuel Singer, 3 HaTechiyah Street, Kfar Saba, Israel

[21] Appl. No.: 285,929

[22] Filed: Dec. 19, 1988

[30] Foreign Application Priority Data

Aug. 12, 1988 [IL] Israel .................................. 87432

[51] Int. Cl.⁵ .................................. A61C 13/28
[52] U.S. Cl. .................................. 433/169; 433/173; 433/174
[58] Field of Search ............... 433/167, 169, 172, 173, 433/174, 175, 176, 177

[56] References Cited

U.S. PATENT DOCUMENTS

| | | | |
|---|---|---|---|
| 1,101,810 | 6/1914 | Otrich et al. | 433/177 |
| 2,644,231 | 7/1953 | Brennan | 433/173 |
| 2,746,146 | 5/1956 | Del Papa | 433/169 |
| 4,253,834 | 3/1981 | Staubli | 433/177 |
| 4,713,004 | 12/1987 | Linkow et al. | 433/174 |
| 4,854,872 | 8/1989 | Detsch | 433/173 |

FOREIGN PATENT DOCUMENTS

| | | | |
|---|---|---|---|
| 8502337 | 6/1985 | PCT Int'l Appl. | 433/174 |
| 2199626 | 7/1988 | United Kingdom | 433/174 |

Primary Examiner—Cary E. Stone

[57] ABSTRACT

An osteointegrated implant comprises a shank formed with external threads at one end receivable in a bone formed in the jawbone; a cap at the opposite end of the shank and formed with an apertured end wall, to which cap a crown, bridge or denture is securable; a threaded pin threadable into the opposite end of the shank through the apertured end wall of the cap and having an enlarged head for removably securing the cap to the shank; and a shock-absorber spring interposed between the cap and the opposite end of the shank to absorb mastication forces applied to the crown, bridge or denture when secured to the cap.

17 Claims, 3 Drawing Sheets

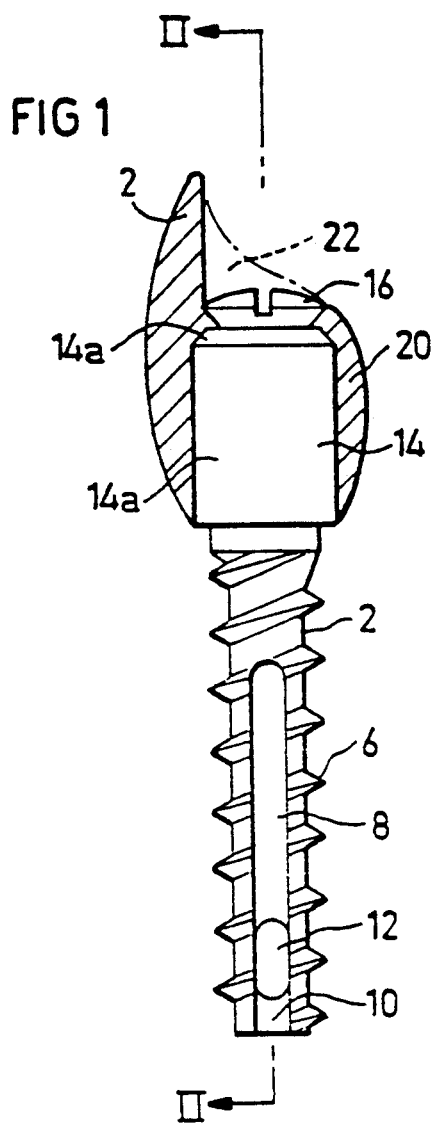
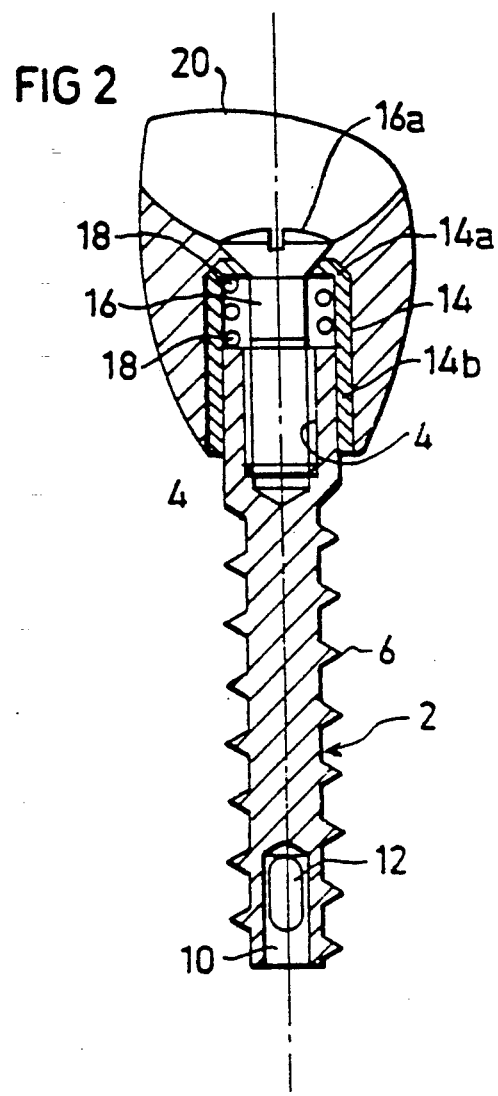
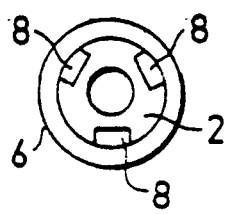

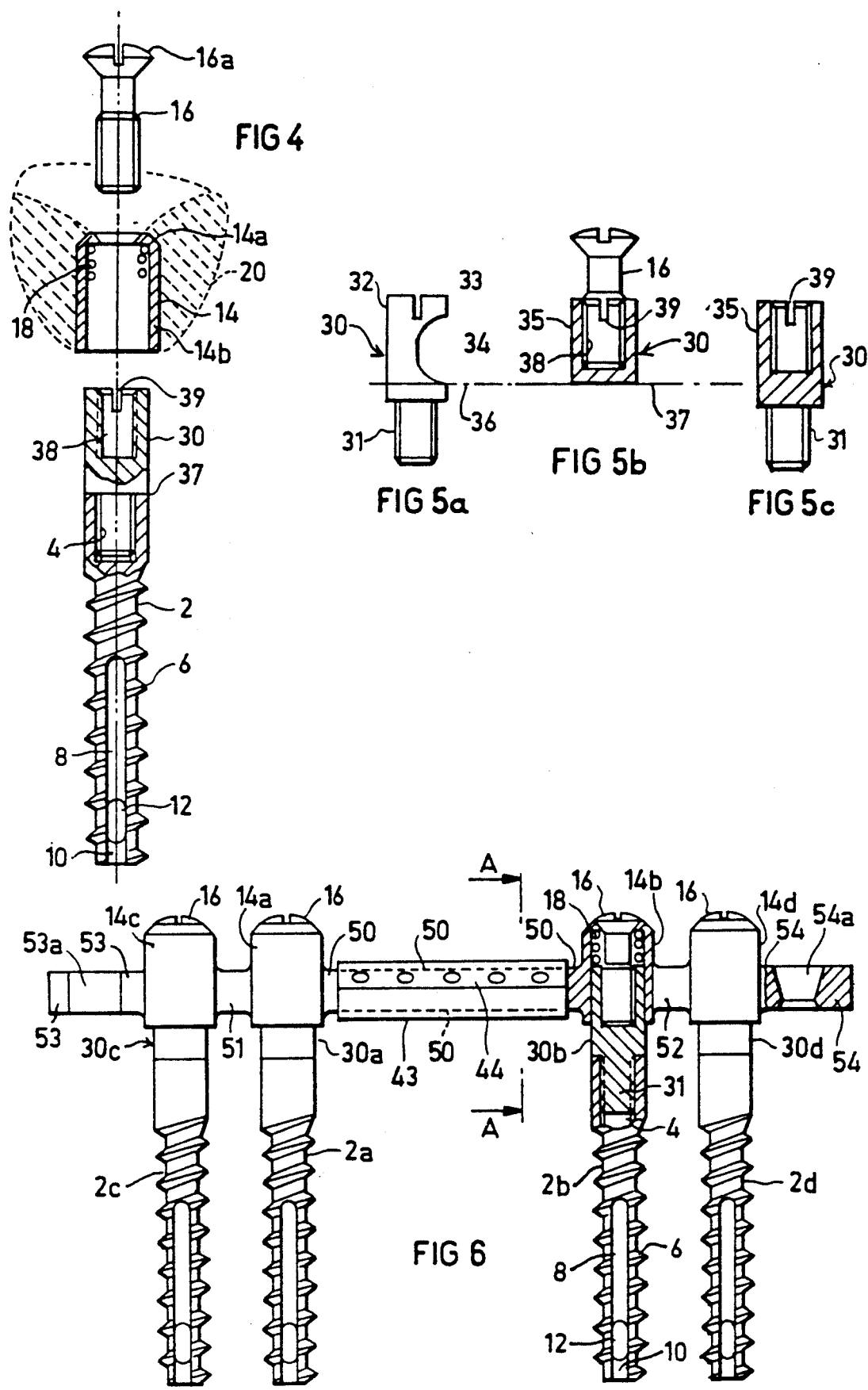

OSTEOINTEGRATED IMPLANTS AND DENTAL IMPLANT ASSEMBLIES

BACKGROUND OF THE INVENTION

The present invention relates to osteointegrated implants and implant assemblies for implantation into the jawbone of a person in order to secure crowns, bridges or dentures.

Removable dentures, commonly used to replace missing natural teeth, are generally uncomfortable to the user. For these reasons, various types of arrangements have been proposed involving implantable posts for implantation into a person's jawbone in order to secure an artificial tooth or a denture containing a plurality of teeth, but efforts are continuously made to improve such arrangements in order to more closely approach the comfort of natural teeth.

An object of the present invention is to provide a new type of implantable post (osteointegrated implant) for implantation into a person's jawbone in order to better secure a crown or a bridge. Another object of the invention is to provide an implantable post assembly including a plurality of implantable posts for securing a denture in a manner which is more comfortable to the user, enables better fitting to the user's mouth, and permits frequent removal for proper cleaning.

BRIEF SUMMARY OF THE INVENTION

According to the present invention, there is provided an osteointegrated implant for implantation into the jawbone of a person in order to secure a crown, bridge or denture thereto, comprising: a shank formed with external threads at one end receivable in a bore formed in the jawbone; a cap at the opposite end of the shank and formed with an apertured end wall, to which cap the crown, bridge or denture is securable; and a threaded pin threadable into the opposite end of the shank through the apertured end wall of the cap and having an enlarged head for securing the cap to the shank.

According to further features, the osteointegrated implant further includes a shock-absorber spring interposed between the cap and the opposite end of the shank to absorb mastication forces applied to the crown, bridge or denture when secured to the cap. The opposite end of the shank is of cylindrical configuration, and the cap has a cylindrical side wall enclosing the opposite end of the shank with a small clearance to permit some lateral as well as axial movement of the cap with respect to the shank.

According to further features in the preferred embodiments of the invention described below, the outer face of the threaded end of the shank is further formed with a blind bore starting from its threaded end and extending a short distance axially thereof permitting tissue growth therein for enhancing the anchoring of the implant in the jawbone; preferably, also, the shank is further formed with a blind bore starting from its threaded end and extending a short distance thereof, and a transversely-extending bore through the threaded end, permitting tissue growth for further enhancing the anchoring of the implant in the jawbone.

In one described embodiment, the opposite end of the shank includes a socket receiving the threaded pin. In a second described embodiment, the opposite end of the shank includes a socket, and a correction adaptor formed at one end with a threaded stem threaded into the socket, and at the opposite end with another threaded socket receiving the threaded pin.

The described osteointegrated implant may be used in combination with a crown or bridge secured to the cap by a dental adhesive which covers the head of the pin.

Also described is the use of the osteointegrated implant as part of an implant assembly comprising at least two such osteointegrated implants, prefereably four, joined together by bars secured to the caps of the implants.

As will be described more particularly below, an osteointegrated implant constructed in accordance with the foregoing features of the invention may be used to secure a crown or a bridge or, when incorporated in an assembly of a plurality of posts, may be used to secure a denture of a set of teeth, in a manner which enables a more precise fit to be made to the user's mouth, permits frequent removal for proper cleaning, and generally approaches the comfort of natural teeth.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a side elevational view illustrating one form of osteointegrated implant, containing a crown secured thereto, constructed in accordance with the present invention;

FIG. 2 is a longitudinal sectional view along line II—II of FIG. 1;

FIG. 3 is a bottom view of the implant of FIGS. 1 and 2;

FIG. 4 is an exploded view of an osteointegrated implant similar to the construction of FIGS. 1-3 but including a correction adaptor to enable a more precise fit to be made to the user's mouth;

FIGS. 5a-5c illustrate the manner of constructing a correction adaptor for use in the osteointegrated implant of FIG. 4;

DESCRIPTION OF PREFERRED EMBODIMENTS

Figure 6A:
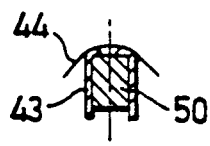
FIG. 6 is a side elevational view, partly in section, illustrating an osteointegrated implant assembly constructed in accordance with the present invention for removably securing a denture, FIG. 6a being a sectional view along line A—A of FIG. 6, and FIG. 6b being a fragmentary view illustrating a detail in the construction of the assembly of FIG. 6 and the manner by which it cooperates with the denture to be secured thereto.

With reference first to FIGS. 1-3, there is illustrated an osteointegrated implant comprising a shank 2 formed with a socket 4 at its upper end, and with a spiral thread 6 on the outer face of its lower end. The threaded end of shank 2 is further formed with three recesses 8 extending axially of the shank, starting at its lower end and terminating short of its socket 4. A blind bore 10 is formed in shank 2 starting from its lower end and extending axially a short distance; and a further bore 12 is formed through the lower end of the shank to extend transversely through the shank and its axial bore 10.

Shank 2 is of cylindrical configuration, and its socket 4 is closed by a cap 14 formed with an apertured end wall 14a and with a cylindrical side wall 14b. Cap 14 is secured to the shank by a threaded pin 16 threadable through the apertured end wall 14a of cap 14 and into socket 4 of the shank, pin 16 being formed with an enlarged head 16a securing the cap to the shank. A coiled spring 18 is interposed between the upper edge of shank 2 and the apertured end wall 14a of cap 14. A crown 20 is secured to cap 14 by threaded pin 16 and by an adhesive dental cement 22, for example, an acrylic adhesive.

Spring 18 between the end of shank 2 and the cap end wall 14a serves as a shock absorber spring to absorb mastication forces applied to the artificial tooth 20. The outer face of the end of shank 2 formed with socket 4 is of slightly smaller diameter than the inner face of the cap side wall 14b so as to provide a small clearance permitting some lateral, as well as axial, movement of the cap 14 and the artificial tooth 20 secured thereto, with respect to the shank.

The implantable tooth illustrated in FIGS. 1-3 is applied to the patient in the following manner:

First, the threaded shank 2 is threaded into the patient's jawbone up to the juncture of the threads 6 with the lower end of socket 4. A screw (not illustrated) having a flattened head, is inserted into socket 4 such that the head of the screw is situated below the upper level of the gums. The purpose of the screw is to prevent entry of tissue into socket 4. The gums are then sutured closed, and the implant allowed to set for a period of several months, about 4-6 months if implanted into the lower jaw, and about 8-10 months if implanted into the upper jaw. The bone tissue of the upper jaw is less dense than that of the lower jaw which accounts for the longer setting period required for the upper jaw. During the setting period, the bone tissue fills the recesses 8, and bores 10 and 12, thereby firmly anchoring the shank 2 in the patient's jawbone.

Following the setting period, the gums are reopened, the flat-headed screw removed, and the correction adaptor 30, as described below with respect to FIGS. 4 and 5a-5c, is inserted into socket 4. Measurements are taken with respect to the correction adaptor 30 which is then removed. Another screw (not illustrated) having the outer configuration of cap 14 and longer than the flat-headed screw, is inserted into socket 4 such that its head protrudes above the upper level of the gums. This screw is left in the patient's mouth for about 1-2 weeks and it functions to prevent reclosure of the gums and it allows the gums to set to the dimensions of the implant. The measurements taken with respect to the correction adaptor are taken both as to the angle and degree of projection of the socket end 4 of shank 2 from the patient's jawbone to determine whether the osteointegrated implant is properly aligned with the patient's mouth.

The correction adaptor 30 is then adjusted to achieve precise alignment as is described below with respect to FIGS. 4, 5a-5c, and is connected to cap 14. The protruding gum-setting screw is then removed and the precisely aligned correction adaptor 30 connected to cap 14 to which is attached the crown 20 and spring 18 is then secured into socket 4 at the end of shank 2 by pin 16, and sealing plastic material 22 is then applied to cover the head 16a of pin 16.

Thereafter, the crown 20 and its cap 14 may be removed in a similar manner whenever necessary for similar adjustment and/or special cleaning.

FIG. 4 illustrates an osteointegrated implant constructed as described above with respect to FIG. 1-3 but including a correction adaptor, generally designated 30, to correct for angle and/or projection of the implant, during the setting period of several months, in order to precisely fit the crown to the mouth of the patient; whereas FIGS. 5a-5c illustrate the manner of constructing the correction adaptor 30 illustrated in FIG. 4.

The osteointegrated implant illustrated in FIG. 4 is of the same construction as described above with respect to FIGS. 1-3, and therefore its various parts are identified by the same reference numerals, except that the correction adaptor 30 is included in the socket 4 end of shank 2 between that end of the shank and the cap 14 carrying the crown 20.

The implant is applied to the patient's jawbone in the same manner as described above with respect to FIGS. 1-3 without correction adaptor 30, and is permitted to set for the several-months period when the shank 2 is firmly anchored to the jawbone. After this setting period, measurements are taken to determine the correction, if any, required to be made with respect to the angle and projection of the upper end of shank 2 in order to provide a precise fit of the crown in the patient's mouth. Thus, after the end of the setting period (e.g., 4-6 months for the lower jaw and 8-10 months for the upper jaw), the flat-headed screw is removed in the same manner as described above with respect to FIGS. 1-3, and the correction adaptor 30 illustrated in FIG. 5a is inserted into socket 4 of the shank 2. For this purpose, correction adaptor 30 includes a threaded stem 31 threaded into socket 4, and an upper end 32 formed with a screwdriver slot 33 for threading the adaptor into the socket 4. Correction adaptor 30 is further formed with a semi-cylindrical slot 34 to provide precise orientation of the correction adaptor 30 when inserted into socket 4 of the implanted shank 2.

Impressions are then made and the required corrections in both the angle and projection are then determined.

Correction adaptor 30 is then removed from the implanted shank, and another piece 35, illustrated in FIG. 5b, is cut at the required angle and length so that, when the upper part 32 of the correction adaptor 30 of FIG. 5a is cut to provide a complementary mating surface, any misalignment in angle and projection of the implanted shank 2 will be corrected. The correction adaptor 30 is then cut along a line, e.g., as shown at 36. Correction piece 35 is similarly cut along a complementary line, as shown at 37, and is attached, as by welding or brazing, to the remainder of correction adaptor 30 replacing the removed part 32 originally included in the correction adaptor. Thus, the composite adaptor, when inserted into socket 4 of shank 2, will correct for any misalignment in angle or projection in order to provide a precise fit of the implanted shank 2 within the patient's mouth.

As shown in FIG. 5b, the added piece 35 of the correction adaptor 30 is formed with a socket 38 for receiving the pin 16, and also with a screwdriver slot 39 so as to permit the composite adaptor, as illustrated in FIG. 5c, to be inserted into socket 4 of the implanted shank 2 in order to correct for any misalignment of the shank after it has become firmly anchored into the patient's jawbone during the setting period. The cap 14, spring 18, and crown 20, are then attached to the correction adaptor 30 by means of pin 16, as described above with respect to FIGS. 1-3, and may be similarly removed whenever desired for special cleaning (not routine cleaning), polish, repair and/or further adjustment as also described with respect to FIGS. 1-3.

Figure 6B:
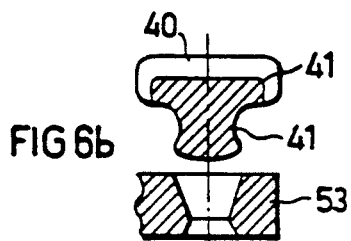
Figure 7:
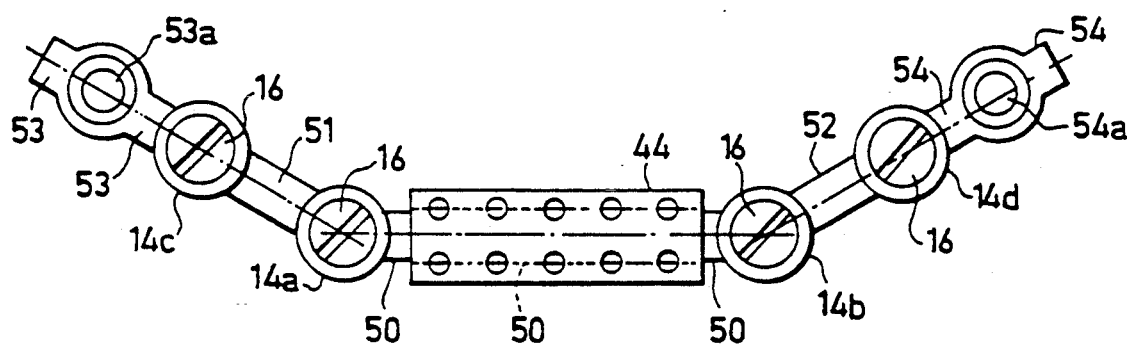
FIG. 7 is a top plan view of the implant assembly of FIG. 6.
Figure 8:
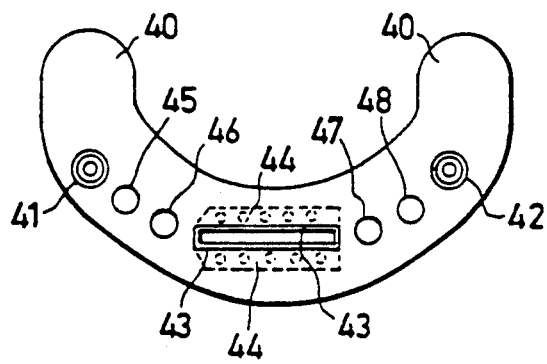
FIG. 8 is a bottom plan view of the denture showing the parts cooperable with the implant assembly of FIGS. 6 and 7 for removably securing the denture to the implant assembly.

FIGS. 6-8 illustrate the manner of using the osteointegrated implant construction described above for securing a denture including a set of teeth, rather than a single tooth as described above with respect to FIGS. 1-4. When so used, a plurality of the implants illustrated in FIGS. 1-4 are constructed in the form of an assembly joined together by bars secured to the caps of the implants, and the so-implanted assembly is provided with complementary snap-action parts cooperable with snap-action parts provided on the denture. Such an assembly is illustrated in FIGS. 6 and 7, and the denture attachable thereto is illustrated in FIG. 8. Each of the implants in the assembly of FIGS. 6 and 7 is constructed in the same manner as described above with reference to FIG. 4, including the correction adaptor illustrated in FIGS. 5a-5c, the parts being identified by the same reference numerals, except that the caps 14 for each of the implants in the assembly do not include the crown 20; rather, the implanted post assembly includes snap-fastener parts cooperable with complementary snap-fastener parts provided on the denture, generally designated 40 in FIG. 8, to permit firm attachment of the denture to the implant assembly and also convenient removal of the denture whenever required for cleaning, repair and/or adjustment purposes.

More particularly, the implant assembly illustrated in FIGS. 6 and 7 includes four implantable shanks 2, consisting of two center shanks 2a, 2b and two outer shanks 2c, 2d, each implanted in the same manner as described above with respect to FIGS. 1-3, and each including a correction adaptor 30a-30d applied to correct for any misalignment in angle or projection of the respective shank after the setting period, as described above with respect to FIGS. 4 and 5a-5c. The two center shanks 2a, 2b are joined together by a long bar 50, attached as by welding or brazing to the inner confronting sides of the caps, whereas the two outer shanks 2c, 2d are joined to the center shanks 2a, 2b by short bars 51, 52 joined in a similar manner to the outer sides of the two center caps 14a, 14b and to the inner sides of the two outer caps 14c, 14d by short bars 51, 52. The implant assembly includes two further short bars 53, 54 joined similarly by welding or brazing to the outer sides of the outer caps 14c, 14d. These latter bars are formed with openings or recesses, as shown at 53a with respect to bar 53 in FIG. 6b, serving as snap-fastener parts for receiving complementary snap-fastener parts 41 carried by the denture 40.

As shown in the sectional view of FIG. 6a, the long bar 50 is of rectangular cross-section and serves as a snap-fastener part for receiving a clamping member 43 projecting from a saddle 44 carried by the denture 40. As shown particularly in FIG. 7, the two center shanks 2a, 2b are implanted in the patient's jawbone in a straight line, whereas the two outer shanks 2c, 2d are implanted in the patient's jawbone to form obtuse angles with respect to the straight line connecting the two center shanks 2a, 2b, so that the implant assembly substantially conforms to the curvature of the patient's jawbone.

The denture, as more particularly illustrated in FIG. 8, is also formed to conform to the curvature of the patient's jawbone. It includes the previously-mentioned snap-fastener pins 41 (and 42) receivable within the snap-fastener openings 53a, 54a of the implant assembly, and the saddle clamp 44 attachable to the long bar 50 of the implant assembly. It further includes a pair of recesses 45, 46 on one side of the saddle clamp, and another pair of recesses 47, 48 on the other side of the saddle clamp, for accommodating the caps 14a-14d of the implant assembly.

Each of the shanks 2a-2d of the implant assembly illustrated in FIGS. 6 and 7 is implanted in the patient's jawbone in the same manner as described above with respect to FIGS. 1-3; and after the setting period, the correction adaptors 30a-30d may be applied in the same manner as described above with respect to FIGS. 4 and 5a-5c to correct for any misalignment in angle or projection in order to provide a precise fit to the patient's mouth. While the shanks 2a-2d remain implanted in the patient's jawbone, the long bar 50 and the short bars 51-54 are secured, as by welding or brazing, to the caps 14a-14d of the implant assembly. The joined-together caps 14a-14d are then connected to the aligned correction adaptors 30a-30d, which are inserted into the shanks 2a-2d. The denture 40 (FIG. 8) may then be applied with its saddle clamp 43, 44 attached to the long bar 50, and with its pins 41, 42 received within snap-fastener openings 53a, 54a of the implant assembly, so as to firmly clamp the denture 40 to the implant assembly, while at the same time permitting convenient removal of the denture whenever necessary for cleaning and/or adjustment purposes in order to assure a precise fit of the denture to the patient's mouth.

While the invention has been described with respect to several preferred embodiments, it will be appreciated that many other variations, modifications and applications of the invention may be made.

What is claimed is:

1. An osteointegrated implant for implantation into the jawbone of a person in order to secure a crown, bridge or denture thereto, comprising:
   a shank formed with external threads at one end receivable in a bore formed in the jawbone;
   a cap at the opposite end of the shank and formed with an apertured end wall, to which cap the crown, bridge or denture is securable;
   a threaded pin threadable into said opposite end of the shank through the apertured end wall of the cap for removably securing said cap to the shank; and
   a shock-absorber spring interposed between said cap and said opposite end of the shank to absorb mastication forces applied to the crown, bridge or denture when secured to said cap;
   said opposite end of the shank being of cyclindrical configuration, and said cap having a cylindrical side wall enclosing said opposite end of the shank with a small clearance to permit some lateral as well as axial movement of the cap with respect to said shank.

2. The osteointegrated implant according to claim 1, wherein the outer face of said threaded end of the shank is formed with one or more axially-extending recesses permitting tissue growth therein for enhancing the anchoring of the implant in the jawbone.

3. The osteointegrated implant according to claim 1, wherein said shank is further formed with a blind bore starting from its threaded end and extending a short distance axially thereof permitting tissue growth therein for enhancing the anchoring of the implant in the jawbone.

4. The osteointegrated implant according to claim 1, wherein said shank is further formed with a transversely-extending bore through the threaded end thereof permitting tissue growth therein for enhancing the anchoring of the implant in the jawbone.

5. The osteointegrated implant according to claim 1, wherein said opposite end of the shank includes a socket receiving said threaded pin.

6. The osteointegrated implant according to claim 1, wherein said opposite end of the shank includes a socket, and a correction adaptor formed at one end with a threaded stem threaded into said socket, and at the opposite end with another threaded socket receiving said threaded pin.

7. The osteointegrated implant according to claim 1, in combination with a crown secured to said cap by a dental adhesive which covers the head of said pin.

8. An osteointegrated implant assembly comprising at least two osteointegrated implants each according to claim 1, joined together by a bar secured to the caps of the two implants.

9. The implant assembly according to claim 8, wherein there are four osteointegrated implants, including two center implants whose caps are joined together by a long bar, and two outer implants, the inner side of the cap of each outer implant being joined by a short bar to the outer side of the cap of one of the center implants.

10. The implant assembly according to claim 9, wherein said long bar is configured to serve as one part of a snap-fastener for receiving another snap-fastener part carried by the denture.

11. The implant assembly according to claim 10, including two further short bars each joined to the outer side of the cap of one of the outer implants, each of said further short bars being formed with one snap-fastener part for receiving another snap-fastener part carried by the denture.

12. The implant assembly according to claim 11, in combination with a denture having a first snap-fastener part removably attached to said long bar of the implant assembly, and two further snap-fastener parts removably attachable to the snap-fastener parts of said two further short bars.

13. The combination of implant assembly and denture according to claim 12, wherein said first snap-fastener part carried by the denture comprises a saddle clamp removably attached to said long bar of the implant assembly.

14. The combination according to claim 12, wherein said two further snap-fastener parts carried by the denture comprises pins removably attachable within sockets formed in each of two further short bars.

15. An osteointegrated implant assembly for implantation into the jawbone of a person in order to secure a bridge or denture thereto, comprising:
   two implants each including a shank formed with external threads at one end receivable in a bore formed in the jawbone;
   a cap at the opposite end of each shank and formed with an apertured end wall, to which cap the bridge or denture is securable;
   a threaded pin threadable into the opposite end of each shank through the apertured end wall of the cap for removably securing the cap the shank;
   a shock-absorber spring interposed between each cap and the opposite end of its shank to absorb mastication forces applied to the bridge or denture when secured to said cap;
   said opposite end of the shank being of cyclindrical configuration, and said cap having a cylindrical side wall enclosing said opposite end of the shank with a small clearance to permit some lateral as well as axial movement of the cap with respect to said shank;
   and a bar secured to the caps of the two implants.

16. The implant assembly according to claim 15, wherein there are four implants, including two center implants whose caps are joined together by a long bar, and two outer implants, the inner side of the cap of each outer implant being joined by a short bar to the outer side of the cap of one of the center implants.

17. The implant assembly according to claim 16, wherein said long bar is configured to serve as one part of a snap-fastener for receiving another snap-fastener part carried by the denture.

* * * * *

UNITED STATES PATENT AND TRADEMARK OFFICE
CERTIFICATE OF CORRECTION

PATENT NO. : 5,082,445

DATED : January 21, 1992

INVENTOR(S) : Shmuel Singer

It is certified that error appears in the above-identified patent and that said Letters Patent is hereby corrected as shown below:

On the title page,

In the Abstract Line 2, "bone" should be --bore--.

Signed and Sealed this

Eighteenth Day of January, 1994

*Attest:*

BRUCE LEHMAN

*Attesting Officer*     Commissioner of Patents and Trademarks